United States Patent
Shukla et al.

(10) Patent No.: US 8,310,243 B2
(45) Date of Patent: Nov. 13, 2012

(54) LOCAL ELECTROCHEMICAL IMPEDANCE SPECTROSCOPY (LEIS) FOR DETECTING COATING DEFECTS IN BURIED PIPELINES

(75) Inventors: Pavan K. Shukla, San Antonio, TX (US); Todd S. Mintz, San Antonio, TX (US); Biswajit Dasgupta, Helotes, TX (US); Jay L. Fisher, Alamo Heights, TX (US); Osvaldo Pensado-Rodriguez, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 352 days.

(21) Appl. No.: 12/853,986

(22) Filed: Aug. 10, 2010

(65) Prior Publication Data

US 2012/0038376 A1  Feb. 16, 2012

(51) Int. Cl.
*G01R 31/08* (2006.01)
*G01R 27/08* (2006.01)

(52) U.S. Cl. .......................... 324/525; 324/700; 324/718

(58) Field of Classification Search .................. 324/525, 324/512, 500, 700, 718, 456, 240
See application file for complete search history.

(56) References Cited

U.S. PATENT DOCUMENTS

| 5,436,565 | A  | * | 7/1995 | Gammell ....................... 324/679 |
| 6,510,038 | B1 | * | 1/2003 | Satou et al. ................... 361/302 |
| 7,341,864 | B2 | * | 3/2008 | Sakamoto et al. .......... 435/285.2 |
| 2003/0169058 | A1 | * | 9/2003 | Pierre et al. ................... 324/700 |
| 2010/0039127 | A1 |  | 2/2010 | Orazem |

FOREIGN PATENT DOCUMENTS

JP   2006300591 A  * 11/2006

* cited by examiner

*Primary Examiner* — Hoai-An D Nguyen
(74) *Attorney, Agent, or Firm* — Chowdhury & Georgakis PC; Ann C Livingston (57) ABSTRACT

A system and associated methods for acquiring and analyzing LEIS data from a buried structure, such as a pipeline. A special probe having adjustable electrodes is placed in the soil above the structure. A voltage is applied to the structure, causing more current to emanate from a coating defect than from intact coating. The probe electrodes acquire a response signal, which is analyzed to detect the defect.

15 Claims, 8 Drawing Sheets

| LOCATION OF HOLIDAY SITES AND THEIR RESPECTIVE LOCATIONS AND SIZES | | |
|---|---|---|
| HOLIDAY NUMBER | LOCATION FROM REFERENCE END OF PIPE (ft) | HOLIDAY SIZE (in x in) |
| 1 | 10 | 5 x 5 |
| 2 | 50 | 6 x 6 |
| 3 | 52 | 1 x 1 |
| 4 | 100 | 5 x 5 |
| 5 | 102 | 2 x 2 |

| TABLE 2. BIELECTRODE PROBE LOCATIONS WITH RESPECT TO THE REFERENCE END OF THE PIPE | | |
| --- | --- | --- |
| SITE NUMBER | LOCATION (ft) | DISTANCE FROM NEAREST HOLIDAY (ft) |
| SITE #1 (AT DEFECT) | 9 | 1 |
| SITE #2 (NO DEFECT) | 31 | 19 |
| SITE #3 (AT DEFECTS) | 48 | 4 |
| SITE #4 (NO DEFECTS) | 75 | 23 |
| SITE #5 (AT DEFECTS) | 100 | $\approx 0$ |

LOCAL ELECTROCHEMICAL IMPEDANCE SPECTROSCOPY (LEIS) FOR DETECTING COATING DEFECTS IN BURIED PIPELINES

TECHNICAL FIELD OF THE INVENTION

This invention relates to detection of coating defects in buried pipelines (or other corrodible buried structures), and more particularly to using local electrochemical impedance spectroscopy for such purposes.

BACKGROUND OF THE INVENTION

Buried pipelines are often coated and/or subjected to cathodic protection (CP) techniques in an effort to mitigate corrosion. However, even the best of today's corrosion avoidance techniques do not prevent corrosion at some point. Coating defects develop and buried pipelines corrode. In the pipeline industry, such defects in the pipeline coating are known as "holidays".

Buried pipelines are not easily accessible for holiday detection. Thus, special techniques have been developed for detecting coating holidays without having to expose the pipe surface.

One approach to detecting coating defects is electrochemical impedance spectroscopy (EIS). EIS methods measure the impedance of a system over a range of frequencies, and therefore the frequency response of the system, including the energy storage (capacitive) and dissipation (resistive) properties, is revealed. Often, data obtained by EIS is expressed graphically in a Bode plot or a Nyquist plot. For pipeline applications, EIS has been studied previously, but many challenges have arisen in analyzing EIS data gathered in field studies.

"Local" EIS (LEIS) is conducted by applying a sinusoidal potential signal (excitation signal) between the pipeline and a buried counter electrode, as with EIS. The response is measured from two reference electrodes (rather than one as in EIS) placed in the soil above a section of the pipeline to detect defects in that section.

DETAILED DESCRIPTION OF THE INVENTION

The following description is directed to an LEIS approach to holiday detection in buried pipelines (or other buried structures with coatings). As stated in the Background, buried structure present particular problems for holiday detection. The term "soil" is used in a most general sense to mean any covering material, typically earth having some degree of moisture.

The LEIS system and methods described herein may be used to identify the location of holidays on a coated buried pipeline, using one or more analysis methods that process data acquired from a bi-electrode probe inserted in the soil along the pipeline. It should be understood that although the description is written in terms of pipelines, the same system and methods could be used for detecting coating defects (holidays) in any corrodible buried structure.

As stated in the Background, pipelines are often coated and/or subjected to cathodic protection, by electrically connecting a structure to be protected with another more easily corroded metal to act as the anode of a simulated electrochemical cell. Another type of cathodic protection technique uses impressed currents; a small current is applied to the buried structure to force the structure surface to act as a cathode with respect to a selected anode.

In general, the invention described herein detects coating defects (holidays) in pipelines, regardless of whether or not the pipeline is under cathodic protection. If the pipeline is under cathodic protection by means of an impressed current, various known techniques can be used to eliminate any cathodic protection effect from the response data.

LEIS Measurement System

Figure 1:
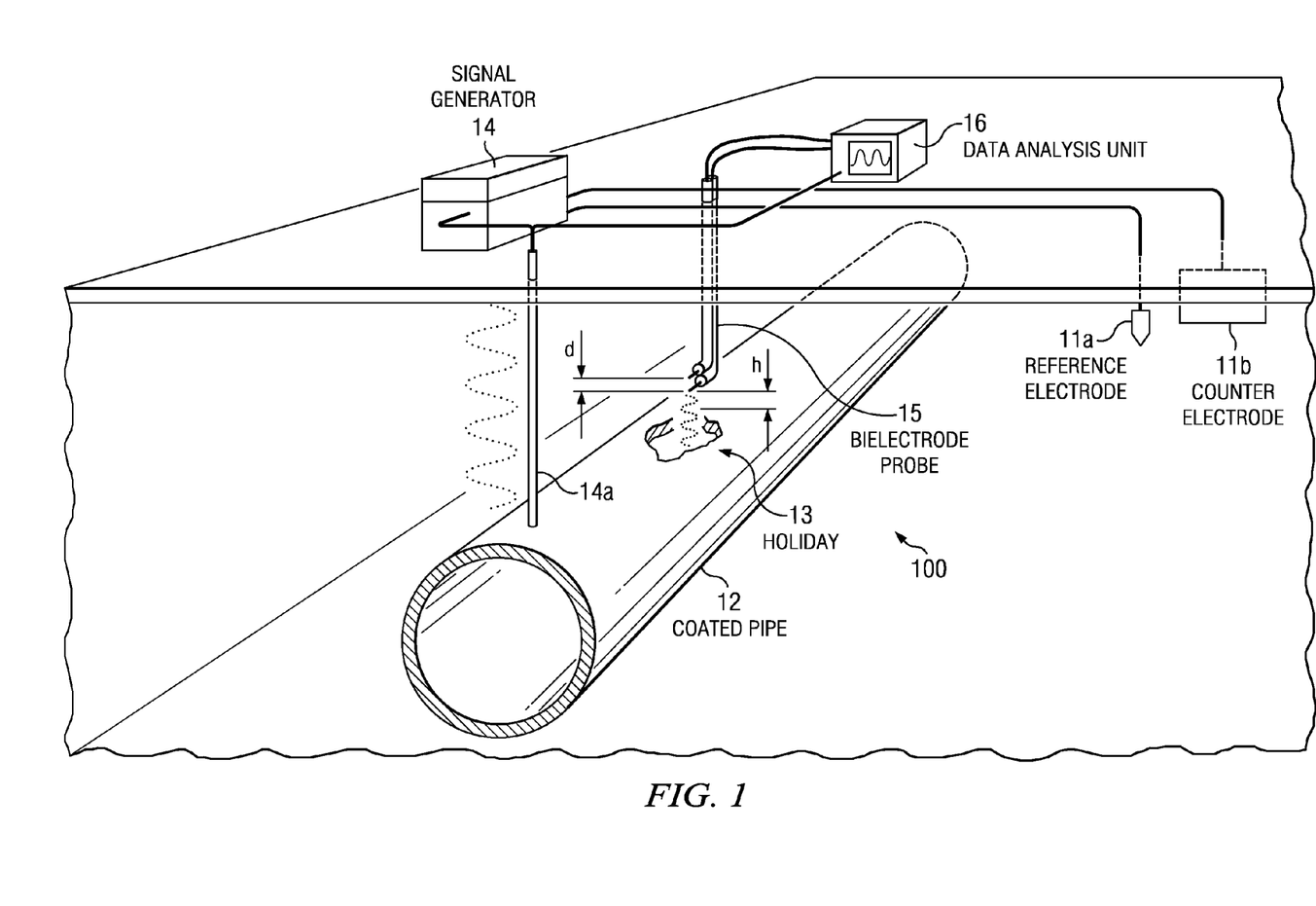
FIG. 1 illustrates an LEIS system for collecting and analyzing LEIS data at different sites above a buried pipeline.

FIG. 1 illustrates an LEIS system 100 for collecting and analyzing LEIS data at different sites above a buried pipeline 12. The pipeline 12 is shown as having a holiday (defect) 13 in its coating.

The basic LEIS system 100 comprises a reference electrode 11a, a counter electrode 11b, a signal generator 14 and connecting rod 14a, and a bi-electrode probe 15. The bi-electrode probe 15 delivers response signals to a data analyzer 16, which may be on-site or remote. As explained below, LEIS system 100 is designed to apply AC excitation signals to the pipeline, and to measure AC response signals in the soil using the bi-electrode probe 15.

The signal generator 14 applies the excitation signal to the coated pipe 12 via an electrical connection, such as a metal rod 14a that touches the surface of the pipeline. Examples of suitable parameters for the applied excitation signal are an amplitude of 1000 mV peak-to-peak and a frequency range of 500 Hz-10000 Hz. In response to the excitation, a current emanates from the pipe surface and coated sections of the pipe. The current emanating through the holiday 13 will be larger because the intact coating on other parts of the pipe will partially shield the current.

The bi-electrode probe 15 is inserted into the ground above the pipe. As further described below in connection with FIG. 2, two probe ends of the bi-electrode probe 15 serve as a pair of electrodes, each establishing an electrical connection with data analyzer 16.

In operation, the probe 15 is placed in an appropriately sized hole above the pipeline. The potential difference between the two electrodes 23 is measured. When the probe 15 is near a holiday 13, the potential difference is greater because of the larger emanating current. Using the calculation described below, response data is processed and analyzed, and the defect is detected. The probe is moved across the ground, into a series of holes over the pipeline, to collect LEIS data at different locations on the pipeline. Alternatively, holes may be dug and probes left in place for permanent monitoring.

Two parameters whose values are optimized for the method are the spacing between the two electrodes (d in FIG. 1) and the minimum proximity of the bottom of probe 15 to the pipe (h in FIG. 1). Other parameters to be optimized are the frequency and amplitude of the current that is applied to the pipe.

Figure 2:
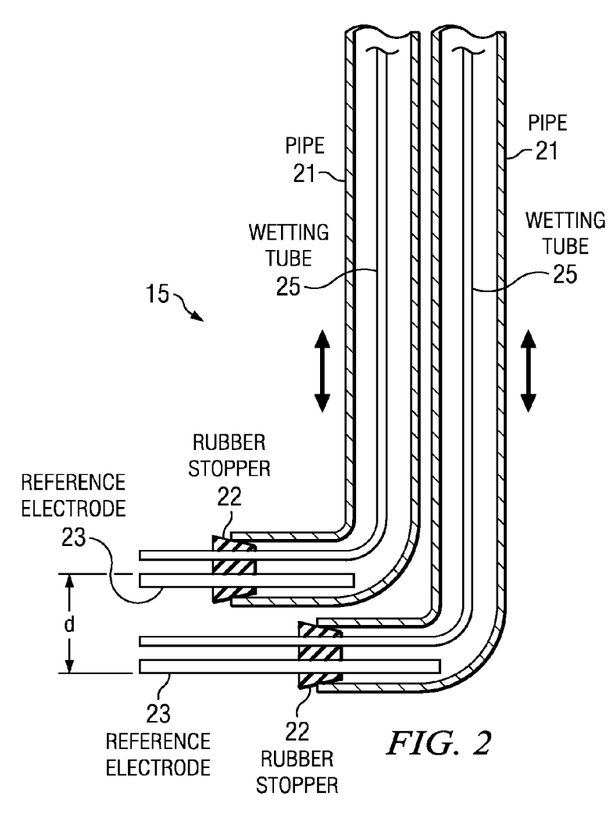
FIG. 2 illustrates the bi-electrode probe of FIG. 1 in further detail.

FIG. 2 illustrates bi-electrode probe 15 in further detail. Probe 15 has two probe elements, each having an L-shaped outer tube 21, a rubber stopper 22, and an electrode 23. The contact ends of the two electrodes 23 are in contact with soil when probe 15 is inserted in the ground.

One or both probe elements may further have a wetting tube 25 extending down the inside length of tube 15, through the stopper 22, with an end open to the soil above the electrode. Wetting tubes 25 are useful if the soil is not sufficiently moist to provide an electrical connection between the electrodes 23 of the bi-electrode probe 15. Water or other conductive liquid may be poured into the wetting tube 25 at the top (above-ground) of upper tube 21 (or both tubes) and flow into the soil above the electrodes 23 and pipeline.

The outer tube 21 is made from a dielectric material, such as PVC. The length of bi-electrode probe 15 is sufficient to permit it to be inserted into the ground and reach an optimum distance from the pipeline, and thus to a large extent, depends on the depth of the pipeline.

Electrodes 23 are a short length of conductive material, and may be "pencil" type electrodes. Such electrodes are available in various configurations. An example of a suitable electrode 23 is a pencil electrode containing a copper (Cu) rod and saturated solution of copper sulfate ($CuSO_4$) in a glass tube, and a porous plug at the end of the glass tube. The porous plug on one end of the tube allows flow of ions from the soil to the copper sulfate electrolyte when the porous plug is in contact with soil.

As indicated in FIG. 2, a typical length of electrodes 23 is 4.5 inches, with about half of that length extending outwardly though the stopper 22. A wire (not shown) extends from each electrode 23, through each pipe 21, to the top of each pipe 21, where appropriate connections are made for wired or wireless communication of response signals to data analyzer 16.

As further indicated in FIG. 2, the tubes 21 are moveable in a vertical direction relative to each other. This permits the distance, d, between the electrodes 23 to be adjusted. Typically, the tubes 21 are attached to each other for stability, but in a manner that permits this vertical movement. For example, the attachment of the tubes 21 to each other may be such that their relative movement is constrained except for movement that allows the contact end of the probe elements to be varied vertically. Typically, the probe separation distance may range from 4 to 12 inches.

Referring again to FIG. 1, data analyzer 16 receives the response signals from the two electrodes 23 of the bi-electrode probe 15. It has appropriate hardware and software to process the data to perform one or more of the various analysis methods described below.

Although signal generator 14 and data analyzer 16 are shown as separate units, these units could be integrated into an automated instrument that would apply a sinusoidal potential to a pipeline, record response signals from the reference electrodes of the bi-electrode probe, and perform appropriate calculations. Also, data analyzer 16 could be separated into a data acquisition unit and processing unit, such that measurement data can be communicated and data processing performed remotely.

Computer Models

A three-dimensional computer model was developed to predict the desired placement of bi-electrode probe 15 with respect to a buried pipeline. More specifically, the computer model was used to determine the pipe-to-soil potential as a function of distance from the pipe towards the ground surface.

The calculated results indicated that 15% of the total potential drop occurs at a distance of 0.5 ft and 33% at a distance of 1 ft from the pipe surface. Therefore, if a sinusoidal signal having a 1000 mV peak-to-peak amplitude is applied to the pipe, the calculated potential directly above a holiday at a distance of 0.5 ft will be 425 mV and at a distance of 1 ft will be 335 mV. This potential is sufficiently large to be measured by the bi-electrode probe 15.

A two-dimensional computer model was developed to determine and understand the effect of holiday size on the local impedance spectrum as a function of the position of the bi-electrode 15 with respect to the holiday 13. The model was developed for a disk electrode system consisting of coated and uncoated sections. It is known that the current distribution generated from a holiday on a pipeline is analogous to the current distribution from a disk electrode; thus, the local impedance spectrum for a holiday on a disk electrode is assumed to be qualitatively similar to one at the pipe surface.

The LEIS response was calculated as a function of the probe's distance from the disk electrode, the probe's position with respect to the holiday, and a parameter K. The parameter K is defined by:

$$K=2\Pi f C_e$$

, where f is the frequency of the applied signal (Hz) and $C_e$ is the capacitance at the electrode and soil interface (Farads/ft2).

The model results were analyzed for a 6 ft radius disk electrode containing a 0.5 in diameter holiday at the center of the disk. The disk electrode was placed 5 ft below the ground surface. The local impedances for bi-electrode probe positions of 0.0 and 0.5 ft from the center of the disk electrode and 1 ft vertically above the disk electrode were calculated.

The following observations were obtained from the simulation:

(1) The frequency of the applied signal should be less than 0.1 mHz to produce significant differences in local impedances of the coated surface and the holiday. The value of K for this frequency is $10^{-2}$ and is based on the measured capacitance of a cathodically polarized carbon steel rod in soil, which is on the order of 100 $\mu F/ft^2$ for an area of 1 $cm^2$.

(2) For applied frequencies of 0.1 mHz or greater, the differences in the local impedances of the holiday and coated sites were due only to the resistivity of the coatings.

Thus, a holiday can be distinguished from a coated site because the resistive path to the current from a holiday is less than that of a coated material.

Field Measurements

Field measurements were conducted using an asphaltic-coated, 6 inch diameter buried pipe. The pipe was 120 ft long and approximately 3.3 ft underground. For test purposes, four taped, insulated risers extended above the soil surface at locations of 0, 20, 60, and 120 ft from a reference end of the pipe.

Figure 3:
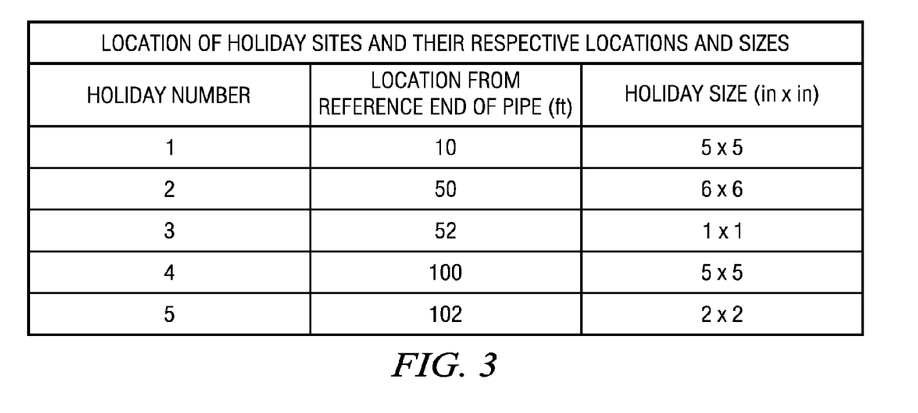
FIG. 3 lists the locations of the holidays on a test pipeline, with respect to a reference end of the pipe.

Also for test purposes, prior to the pipeline being buried, five holidays were created at specific locations along the pipe. FIG. 3 lists the locations of the holidays with respect to the reference end of the pipe.

In the gas and oil transmission pipeline industry, closed interval surveys are routinely conducted to identify holiday locations on buried pipelines under CP using pipe-to-soil potential measurements at the ground surface directly above the pipeline. To demonstrate that the holidays on the test pipe could not be detected using a closed interval survey, the above-ground pipe-to-soil potential was measured directly above the pipe after the holidays were created.

Figure 4A:
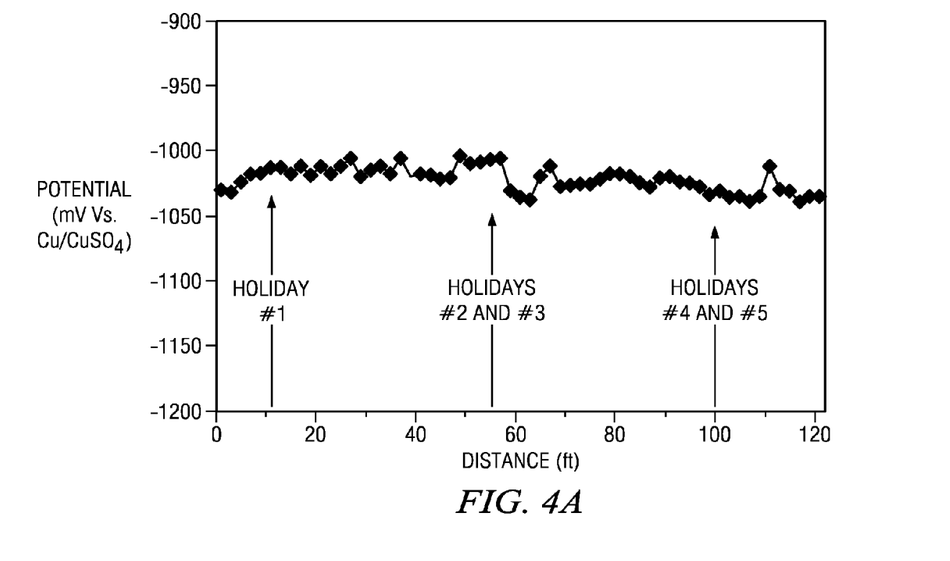
FIGS. 4A and 4B illustrate pipe-to-soil potentials measured with respect to a Cu/CuSO$_4$ electrode for applied signals of −1000 mV and −850 mV, respectively, using a closed interval survey method for the test pipeline.
Figure 4B:
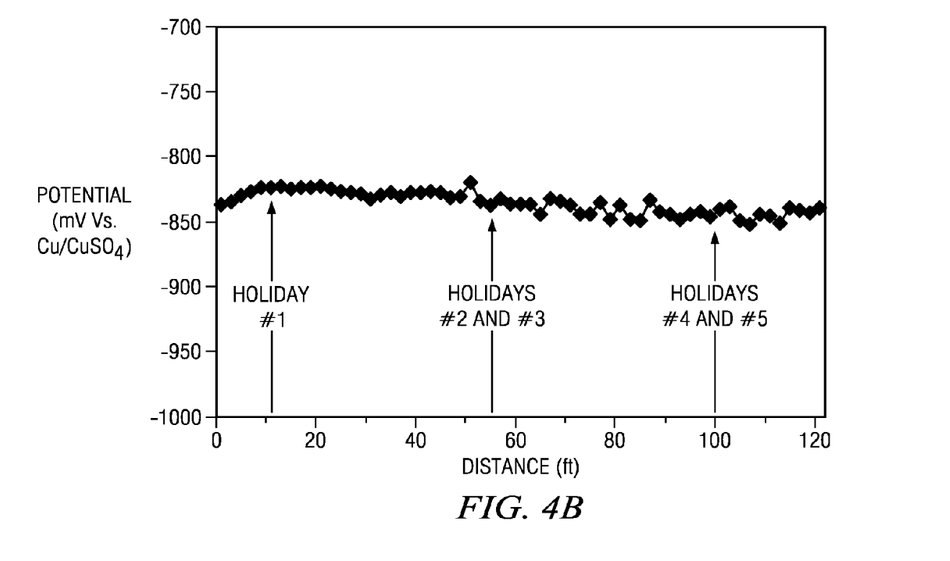

FIGS. 4A and 4B illustrate pipe-to-soil potentials measured with a Cu/CuSO$_4$ electrode for applied signals of −1000 mV and −850 mV, respectively, using a closed interval survey. The measurements were made to the test pipeline described in FIG. 3, directly above the pipeline. As illustrated, there are no systematic differences in pipe-to-soil potentials between the coated sections and holiday sites. Thus, referring to FIGS. 3, 4A, and 4B, it is clear that the closed interval survey was not able to detect holidays as large as 6×6 inches.

Figure 5:
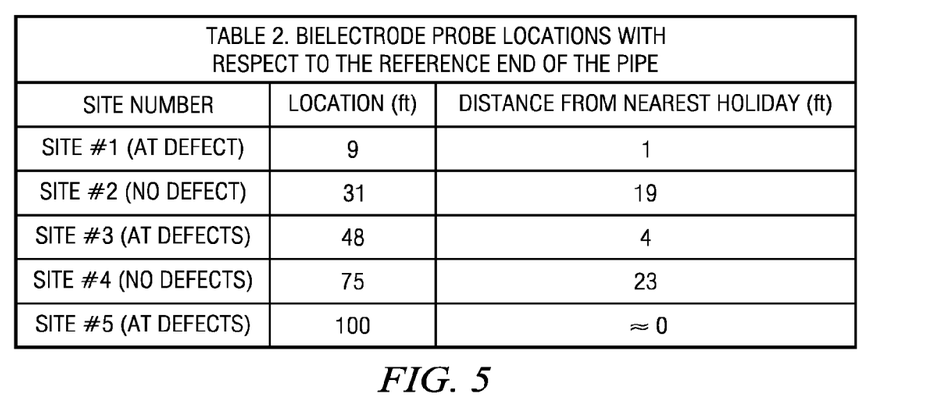
FIG. 5 sets out locations of the bi-electric probe when used for LEIS detection of holidays on the test pipeline.

FIG. 5 sets out locations of bi-electric probe 15 when used for LEIS detection of the same test pipeline. By referring to FIG. 3, and as shown in the last column of FIG. 5, the distance of the probe 15 from each test defect is known.

The electrodes 23 of probe 15 were Cu/CuSO$_4$ electrodes. The pipe was buried and LEIS measurements were conducted by inserting the probe 15 as close to the pipe as possible at the specified locations. LEIS data were collected for probe separation distances of 4 in and 12 in. The pipe was subjected to a sinusoidal potential of 1,000 mV peak-to-peak.

The amplitudes of the response signals corresponding to the applied frequency were calculated using a Fast Fourier Transform (FFT), which decomposes the response signal into frequency based components. The measured amplitudes of the response signals at a frequency equal to the frequency of the applied excitation signal is used to calculate the potential difference between the two electrodes 23 of the bi-electrode probe 15.

The calculated potential differences were then used to calculate local impedances according to the following equation:

$$Z_{local}(f) = \frac{V_{applied,amp}(f)d}{\Delta\Phi_{amp}(f)\kappa} \quad (2)$$

$Z_{local}(f)$ calculated local electrochemical impedance ($\Omega\text{ft}^2$) at frequency f (Hz)

$V_{applied,amp}$ amplitude of the applied voltage signal (V) at frequency f (Hz)

$\Delta\Phi_{amp}$ amplitude difference in voltage (V) of the response signals between the two electrodes of the bi-electrode probe at the frequency f (Hz) of the applied signal d bielectrode probe electrode separate (ft)

κ conductivity of soil=1000 $\Omega^{-1}\text{ft}^{-1}$

Figure 6A:
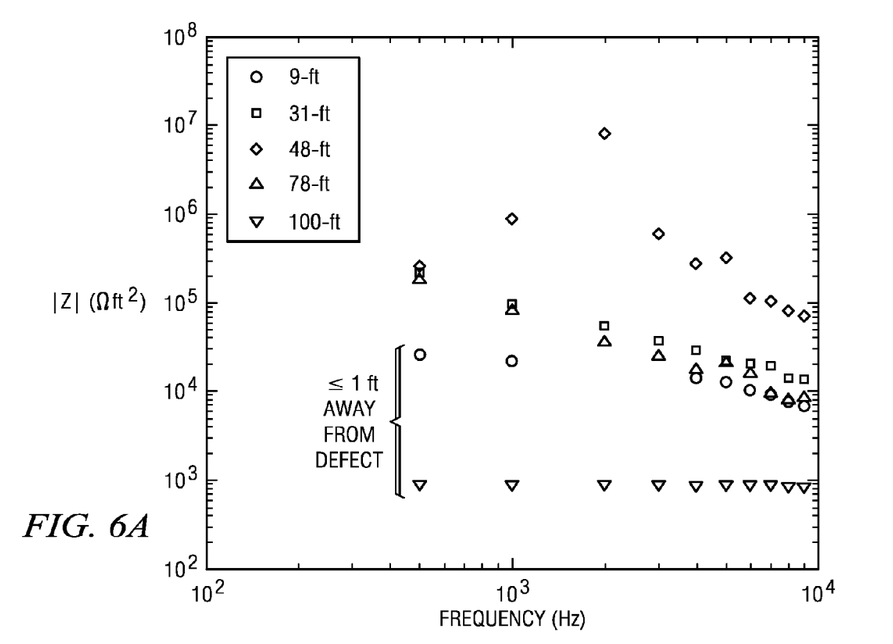
FIGS. 6A and 6B illustrate calculated electrochemical impedances for probe separation distances of 4 in and 12 in, respectively, as a function of the frequency of the applied signal.
Figure 6B:
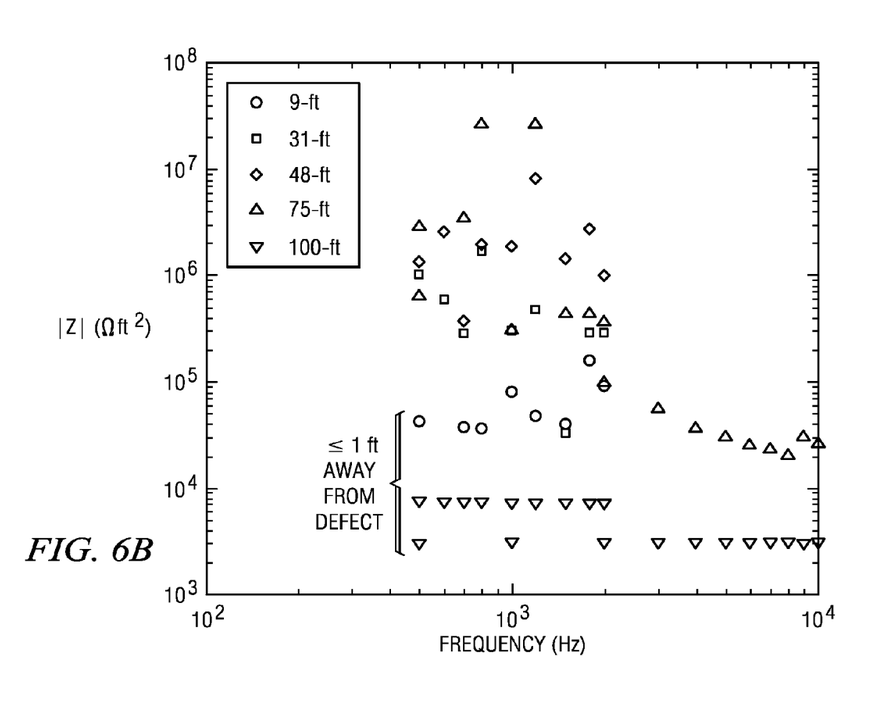

FIGS. 6A and 6B illustrate the calculated electrochemical impedances, $Z_{local}(f)$, for probe separation distances of 4 in and 12 in, respectively, as a function of the frequency of the applied signal. Each figure shows the electrochemical impedance spectra for different probe locations along the length of the pipeline.

Referring again to FIG. 5, as well as to FIGS. 6A and 6B, for the probe locations at 9 ft and 100 ft, the bioelectric probe 15 was less than 1 ft from holidays. The local impedances for the bioelectric probe locations at 9 ft and 100 ft are significantly lower than for other probe locations, especially for larger electrode separation distance (FIG. 6B).

FIGS. 6A and 6B show that the local impedance at a position within 1 ft of a holiday site are significantly lower than the impedance measured at a minimum of 4 ft from a holiday. In general, the data obtained at 100 ft and 9 ft from the reference end of the pipe have lower impedances than the other locations. The bi-electrode probe located at 100 ft from the reference end of the pipe was directly above a holiday and showed the lowest impedance of all locations. The bi-electrode probe located 9 ft from the reference end of the pipe was 1 ft away from the holiday and was discernable when a probe separation distance of 12 in was used. Because of the relationship between impedance and voltage, the low impedance values indicate a high potential difference at the locations near the holidays.

Analysis Alternatives

Figure 7A:
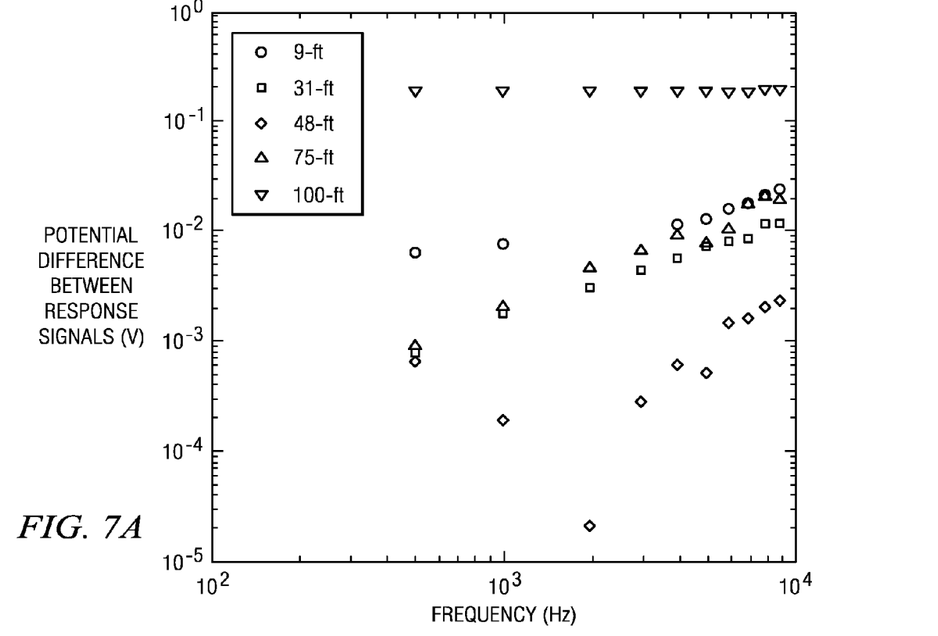
FIGS. 7A and 7B illustrate calculated potential differences for probe separation distances of 4 in and 12 in, respectively, as a function of frequency of the applied signal.
Figure 7B:
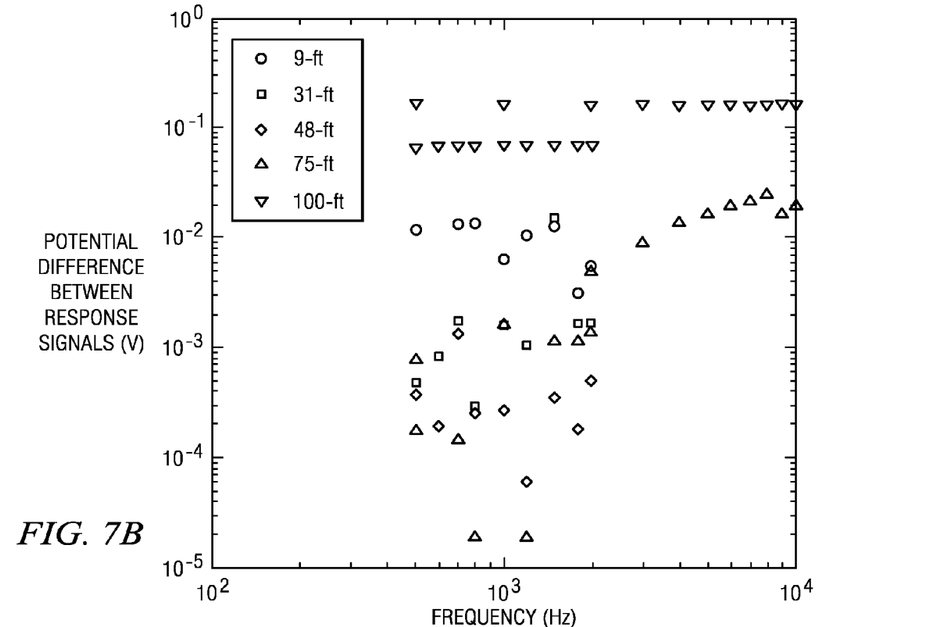

FIGS. 7A and 7B illustrate that that calculations for detecting holidays can be further simplified. As described above, the amplitudes of the response signals may be calculated using Fast Fourier Transforms (FFTs). These amplitude values are then used to calculate the potential difference between the bottom and top reference electrodes of the bielectrode probe, $\Delta\Phi_{amp}$.

FIGS. 7A and 7B illustrate the calculated potential differences versus frequency of the applied signal, for probe separation distances of 4 in and 12 in respectively. As illustrated, and in a manner similar to FIGS. 6A and 6B, the potential differences are dependent upon the probe placement position. As shown in FIG. 7A, the potential differences for the 100 ft site are larger than differences at other sites for all frequencies. Since the bi-electrode probe was directly placed above the 100 ft site where a holiday is located, a larger current is expected to flow through the soil region adjacent to the holiday, compared to other sites. As a result the potential drop between reference electrodes of the bielectrode probe at the 100 ft site is largest. The same result is observed for the bi-electrode probe separation distance of 12 in.

As shown in FIG. 7A, the potential differences for the 9 ft site are higher than all sites other than the 100 ft site. In this case, the bi-electrode probe was located approximately 1 ft away from the holiday. The same result is observed in the results presented for a probe separation distance of 12 in, as shown in FIG. 7B. This analysis indicates that the potential difference between the response signals can be used an indicator for identifying holiday sites.

Further analysis can be performed by calculating pipe impedances with respect to the response signal from either the top or bottom electrode 23. The pipe impedance is calculated according to the following equation:

$$Z_{pipe}(\omega) = \frac{V_{applied,amp}(\omega)d}{(V_{applied,amp}(\omega) - \Phi_{response,amp}(\omega))\kappa},$$

where $Z_{pipe}(\omega)$ impedance of the pipe ($\Omega\text{ft}^2$) with respect to a response signal at angular frequency ω (rad/sec)

Figure 8A:
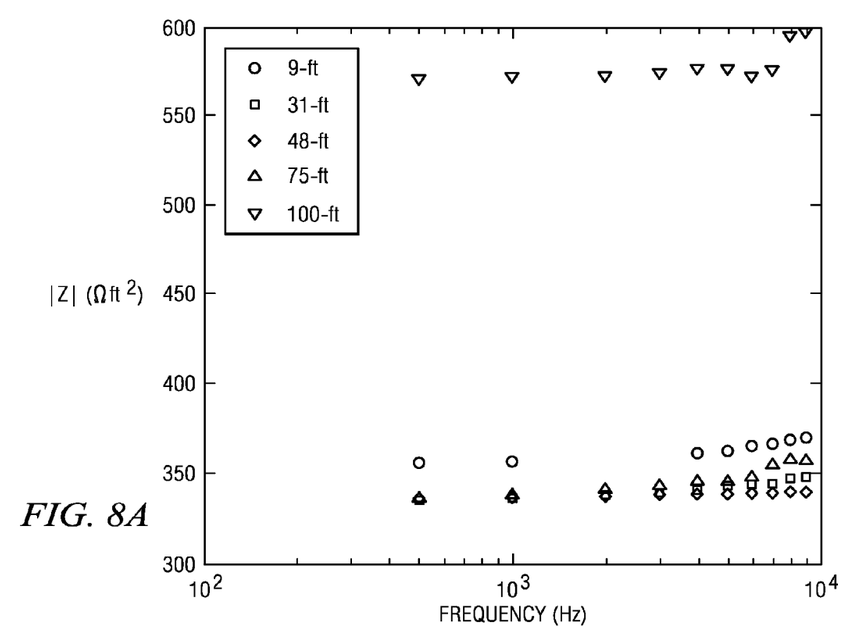
FIGS. 8A and 8B illustrate pipe impedance calculated from the response signal collected at the bottom reference electrode of the bielectrode probe, for the probe separation distances of 4 and 12 in, respectively.
Figure 8B:
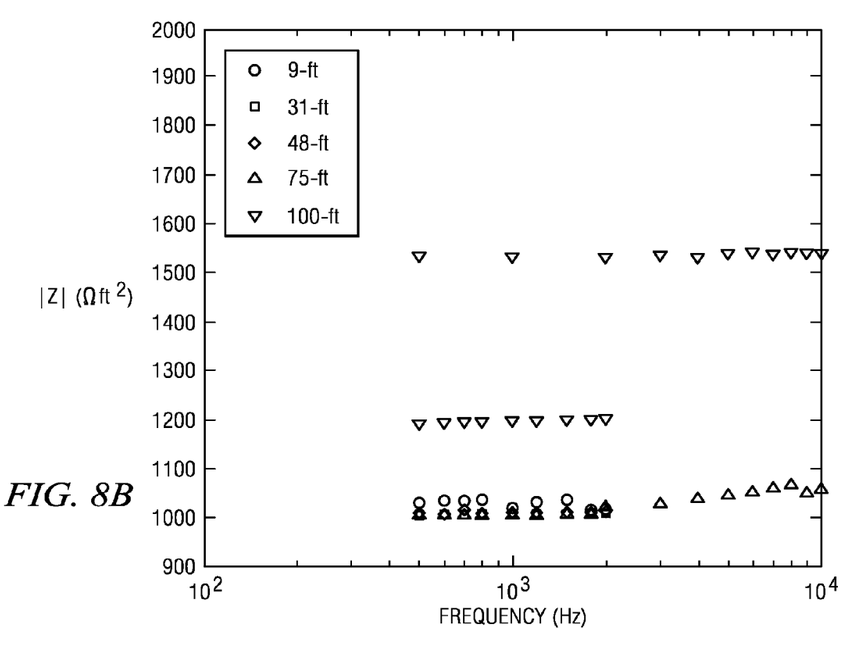

$\Phi_{response,amp}$ amplitude of a response signal (V) at the angular frequency (rad/sec) of the applied signal FIGS. 8A and 8B illustrate the pipe impedance calculated from the response signal collected at the bottom reference electrode of the bielectrode probe, for the probe separation distance of 4 and 12 in, respectively. As seen in the figures, the pipe impedance is higher for the 9 and 100 ft probe locations than for the 31, 48, and 75 ft locations. Thus, this analysis can also be used to identify the holiday sites on a buried coated pipeline.

Calculations similar to those illustrated in FIGS. 8A and 8B may be made for pipe impedance with respect to the response signal collected at the top reference electrode of the bielectrode probe. For a 4 in probe separation, experimental results show that the pipe impedance is higher for the 9 and 100 ft sites than for the 31, 48, and 75 ft sites. However, for the 12 in probe separation, only the pipe impedance at the 100 ft site is higher than the remaining sites. Therefore, only the holiday at the 100 ft site was positively identified for the probe separation distance of 12 in.

Figure 9A:
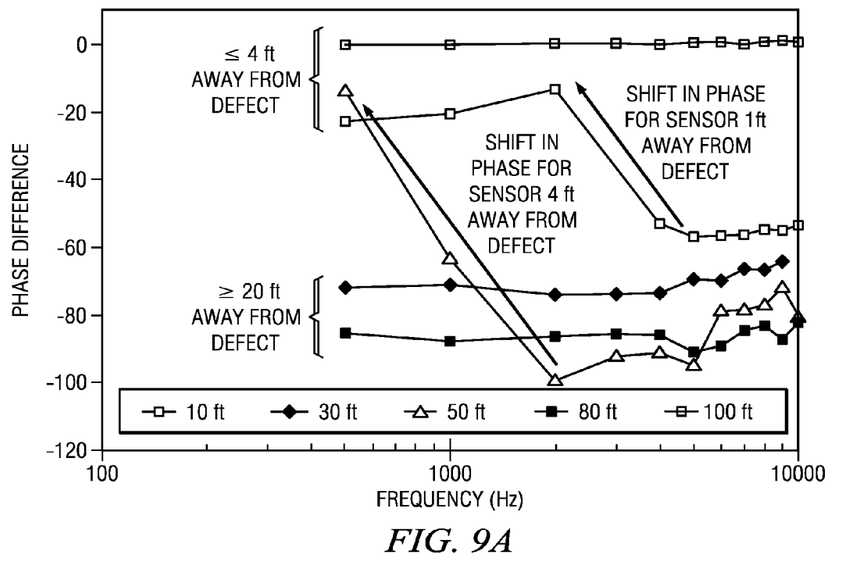
FIGS. 9A and 9B illustrate the calculated results of a phase shift analysis, with probe separation distances of 4 in and 12 in, respectively.
Figure 9B:
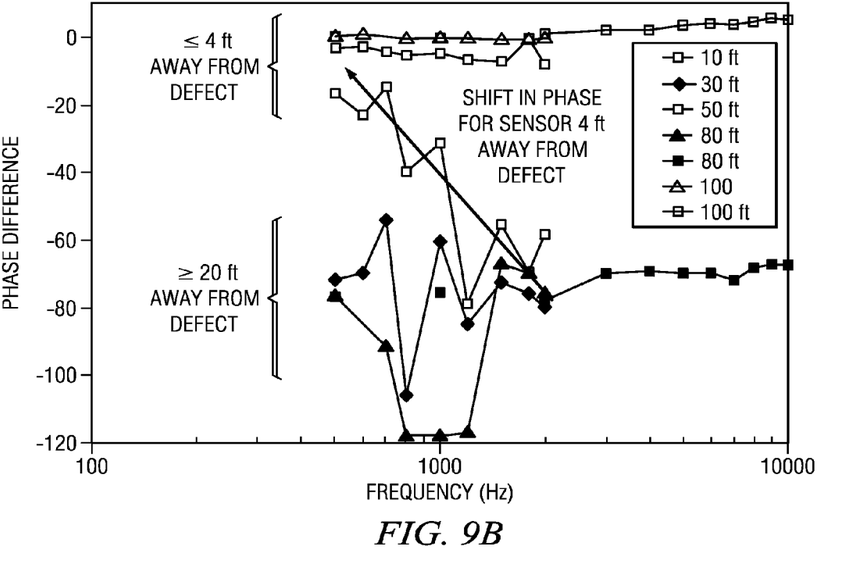

As illustrated in FIGS. 9A and 9B, still further analysis can be performed by calculating the phase shift of the response signals with respect to the applied signal. First, the response signal of the bottom reference electrode (the reference electrode closer to the pipe surface) was subtracted from that of the top electrode (the reference electrode farther from the pipe surface). The phase shift of the resulting response signal was calculated with respect to the applied signal.

FIGS. 9A and 9B illustrate the calculated results of a phase shift analysis, with probe separations of 4 in and 12 in, respectively. These figures are Bode phase plots of the local electrochemical impedance spectra for different probe placement positions. The phase difference of the different sites was calculated considering the difference in amplitude of the response signal between the two reference electrodes of the bioelectric probe.

As illustrated, when the bi-electrode probe is above the defect, there is roughly no phase shift (0 degrees) at a high frequency of 10,000 Hz. However, all other locations have a large (roughly −65 to −90 degree) phase shift. As the frequency is decreased, there is a shift in the phase difference to roughly −10 degrees for measurement locations near a defect. This change of phase shift appears to be dependent upon the distance that a defect is located from the measurement site. For measurements made closer to a defect, the phase shift occurs at higher frequencies. For example, the measurement made at the 9 ft site, which is 1 ft away from a defect, has a phase shift at roughly 4000 Hz as shown in FIG. 9A. However, the measurement at the 50 ft site, which is 4 ft away from a defect, does not have a phase shift until 2000 Hz, as shown in FIG. 9B. There was no change in the phase shift observed for locations that were roughly 20 ft away from a defect. It is possible that the phase shift would have occurred if measurements were made at lower frequencies.

Pattern Recognition Approach to Identify the Presence of Defects from Impedance Signatures The LEIS data, acquired as described above, provides electrical potentials measured at a distance from a buried pipe with a holiday on its coating, as function of frequencies of periodic perturbations in an electrical potential applied to the pipe. The measured electrical potentials can be transformed, according to derived equations, into current responses at a reference electrode and impedance responses as function of the frequency of the input periodic potential applied to the pipe.

Another approach to identify the presence of holidays on coatings in pipes is based on comparing impedance data associated with holidays located at different distances from the measurement point. The impedance data are organized in variations of arrays including magnitudes, phases, and differences between top and bottom electrodes, all as functions of the frequency of the input forcing signal. Pattern recognition is then used to classify impedance signatures (in the form of arrays of data) by similitude. The use of particular arrays differentiates cases where the detecting electrodes are located close to the holiday from cases where the electrodes are far from the holiday. By comparing an array of impedance data to an existing database of impedance responses, it is possible to classify an impedance signal as a close-to-holiday, far-to-holiday, or no-holiday. By collecting more data and further assembling a database of possible impedance responses, it could be possible not only to estimate the distance to the holiday, but also infer holiday features such as placement and size.

An example of a suitable pattern recognition methodology is based on the construction of a self-organizing map (SOM) or Kohonen classifier. A SOM is a 2-dimensional map, in which every pixel is associated with a complete array of impedance data (e.g., impedance and phase versus frequency). Nearby pixels are associated with similar data arrays, and distant pixels correspond to different data arrays. SOMs may be constructed with pixel regions that consistently differentiate close from far holidays. Thus, decision boundaries can be drawn in the SOM to classify impedance signatures into close-to-holiday and far-to-holiday types. By further collection of data, decision boundaries in the SOMs can be refined and used to estimate the distance to the holiday. By carefully designing experiments, accounting for holiday placement and size, SOMs with complex decision boundaries can be developed allowing for fast estimates of holiday features.

What is claimed is:

1. An LEIS method for detecting coating defects in an underground structure buried in soil, comprising:
    placing a bi-electrode probe in the soil above the structure, the bi-electrode probe having two probe tubes, each tube having an in-soil end and an above-ground end, each probe tube having a probe electrode extending from the in-soil end;
    wherein the probe tubes are arranged such that the probe electrodes are vertically spaced when the bi-electrode probe is in place, each probe electrode having a contact end for contacting the soil above the structure;
    wherein at least one of the probe electrodes is moveable with respect to the other such that the vertical distance between the probe electrodes is variable;
    applying a sinusoidal voltage to the structure over a range of frequencies;
    receiving a response signal from each probe electrode;
    processing each response signal to obtain calculated data; and
    analyzing the calculated data to detect the presence of a coating defect.

2. The method of claim 1, further comprising the step of calculating an optimum distance between the probe electrodes and adjusting the distance between the probe electrodes.

3. The method of claim 1, wherein the probe electrodes are adjustable by means of relative vertical motion of the probe tubes.

4. The method of claim 1, further comprising the step of wetting soil between the probe electrodes and the structure by delivering water to the soil via a wetting tube in at least one of the probe elements.

5. The method of claim 1, wherein the processing step is performed by removing the frequency component of the response data, thereby obtaining two sets of amplitude measurement data, one from each probe electrode; and by calculating the difference between the two sets of amplitude measurement data.

6. The method of claim 1, wherein the processing step is performed by calculating pipeline impedance, based on the response signal from only one of the probe electrode.

7. The method of claim 1, wherein the processing step is performed by calculating the difference between the response signals from the probe electrodes, and calculating the phase shift of the resulting data relative to that of the applied signal.

8. The method of claim 1, wherein the processing step is performed using a pattern recognition algorithm.

9. An LEIS system for detecting coating defects in an underground structure buried in soil, comprising:

A signal generator for applying an excitation signal to the pipeline, over a range of frequencies;

a bi-electrode probe in the soil above the structure, the bi-electrode probe having two L-shaped probe tubes, each tube having an in-soil end and an above-ground end, each probe tube having a probe electrode extending from the in-soil end;

wherein the probe tubes are arranged such that the probe electrodes are vertically spaced when the bi-electrode probe is in place, each probe electrode having a contact end for contacting the soil above the structure;

wherein at least one of the probe electrodes is moveable with respect to the other such that the vertical distance between the probe electrodes is variable;

a data analysis unit programmed to receive response signals from the probe electrodes, and to process the response signals to determine whether a coating defect is present.

10. The system of claim 9, wherein the probe electrodes are adjustable by means of relative vertical motion of the probe tubes.

11. The system of claim 9, wherein one or both of the probe tube contains a wetting tube extending from the above-ground end to the in-soil end; wherein the wetting tube has an end open to the soil above one or both electrodes.

12. The system of claim 9, wherein the data analysis unit is programmed to remove the frequency component of the response data, thereby obtaining two sets of amplitude measurement data, one from each probe electrode, and to calculate the difference between the two sets of amplitude measurement data.

13. The system of claim 9, wherein the data analysis unit is programmed to calculate pipeline impedance, based on the response signal from only one of the probe electrode.

14. The system of claim 9, wherein the data analysis unit is programmed to calculate the difference between the response signals from the probe electrodes, and to calculate the phase shift of the resulting data relative to that of the applied signal.

15. The system of claim 9, wherein the data analysis unit is programmed to perform a pattern recognition algorithm.

* * * * *